United States Patent [19]
// Heineke et al.

Patent Number: 6,013,844
Date of Patent: Jan. 11, 2000

[54] PREPARATION OF CATECHOL MONOETHERS AND CATECHOLS

[75] Inventors: Daniel Heineke, Maikammer; Uwe Dingerdissen, Seeheim-Jugenheim; Joachim Wulff-Döring, Frankenthal; Michael Hesse, Worms, all of Germany

[73] Assignee: BASF Aktiengesellschaft, Ludwigshafen, Germany

[21] Appl. No.: 09/115,803

[22] Filed: Jul. 15, 1998

[51] Int. Cl.$^7$ .................................................. C07C 41/00
[52] U.S. Cl. .......................... 568/652; 568/653; 568/772; 568/766; 502/326
[58] Field of Search .................. 568/650, 652, 568/653, 772, 766; 502/326

[56] References Cited

U.S. PATENT DOCUMENTS

| | | | |
|---|---|---|---|
| Re. 29,201 | 5/1977 | McKague | 568/652 |
| 3,682,838 | 8/1972 | Bloch | 502/330 |
| 3,801,651 | 4/1974 | Adolphen et al. | |
| 3,819,719 | 6/1974 | McKague et al. | 260/613 |
| 3,900,522 | 8/1975 | Greco | 568/772 |
| 4,131,628 | 12/1978 | Antos | 585/434 |
| 4,161,614 | 7/1979 | Konz et al. | |
| 4,254,288 | 3/1981 | Gladwin | 568/652 |
| 4,716,143 | 12/1987 | Imai | 502/326 |
| 5,266,171 | 11/1993 | Hermeling | |
| 5,319,148 | 6/1994 | Karcher et al. | |

FOREIGN PATENT DOCUMENTS

| | | |
|---|---|---|
| 951 742 | 7/1974 | Canada . |
| 27 03 077 | 7/1978 | European Pat. Off. . |
| 499 055 | 8/1992 | European Pat. Off. . |
| 2 155 562 | 5/1972 | Germany . |
| 2 064 097 | 7/1972 | Germany . |
| 40 17 576 | 12/1991 | Germany . |
| 1 369 484 | 10/1974 | United Kingdom . |

OTHER PUBLICATIONS

Ind. Eng. Chem., Prod. Res. Dev., vol. 15, No. 3, 1976, Varagnat, Hydroquinone and Pyrocatechol Production by Direct Oxidation of Phenol, 212–215.

*Primary Examiner*—Gary Geist
*Assistant Examiner*—Jean F Vollano
*Attorney, Agent, or Firm*—Keil & Weinkauf

[57] ABSTRACT

A process for preparing catechol monoethers or catechols of the formula Ia or Ib

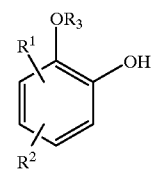

Ia

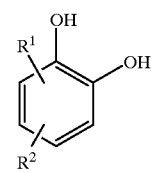

Ib where $R^1$ and $R^2$ are, independently of one another, hydrogen or $C_1$–$C_8$ hydrocarbon radicals, and $R^3$ is a $C_1$–$C_8$ hydrocarbon radical, which comprises a 2-hydroxycyclohexanone dialkyl ketal of the formula II or a 2-alkoxycyclohexanone of the formula III

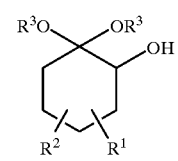

II

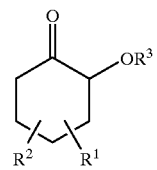

III a) being reacted in the gas phase in the presence of palladium on zirconium oxide as catalyst to obtain compounds Ia or b) carrying out stage a) in the presence of water to obtain compounds Ib.

5 Claims, No Drawings

PREPARATION OF CATECHOL MONOETHERS AND CATECHOLS

The present invention relates to a novel process for preparing catechol monoethers and catechols of the formulae Ia and Ib

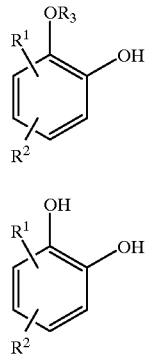

where $R^1$ and $R^2$ are, independently of one another, hydrogen or $C_1$–$C_8$ hydrocarbon radicals, and $R^3$ is a $C_1$–$C_8$ hydrocarbon radical.

Compounds Ia and Ib are known and are used as intermediates for synthesizing drugs, scents and flavorings.

Ind. Eng. Chem., Prod. Res. Dev., 15(3), (1976) 212 describes the catalytic hydroxylation of phenol with hydrogen peroxide in the presence of phosphoric acid and perchloric acid to give catechol and hydroquinone.

However, the disadvantage of this synthetic process is that hydroquinone is obtained in addition to catechol, and in about the same amounts.

Furthermore, DE-A-2 703 077 discloses the conversion of 1,4-cyclohexanedione tetramethyl diketal into hydroquinone dimethyl ether by catalytic dehydrogenation and methanol elimination in the liquid phase.

DE-A-2 064 097 describes a process for preparing catechol and its monoethers by dehydrogenation of corresponding cyclohexanone derivatives at 150–300° C. in the presence of palladium on Li-Al spinel carriers.

EP-A-0 499 055 describes a process for preparing catechol monoethers and catechol by dehydrogenation of 2-hydroxycyclohexanone dimethyl ketal on deactivated platinum metals in the form of supported catalysts. A large number of oxides, sulfates, silicates and, preferably, carbon are mentioned as carriers.

CA 951742 describes the conversion of 2-methoxycyclohexanone into guaiacol on Pd on carbon.

Both the yields and selectivities, and the useful lives of the catalysts are insufficient for industrial use of the processes described above.

It is an object of the present invention to make catechol monoethers Ia and catechols Ib available in a simpler and more economical manner.

We have found that this object is achieved by a process for preparing catechol monoethers or catechols of the formula Ia or Ib

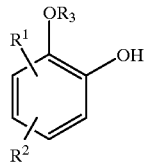

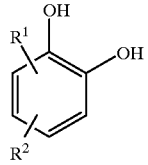

where $R^1$ and $R^2$ are, independently of one another, hydrogen or $C_1$–$C_8$ hydrocarbon radicals, and $R^3$ is a $C_1$–$C_8$ hydrocarbon radical, which comprises a 2-hydroxycyclohexanone dialkyl ketal of the formula II or a 2-alkoxycyclohexanone of the formula III

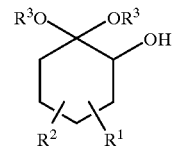

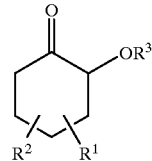

a) being reacted in the gas phase in the presence of palladium on zirconium oxide as catalyst to obtain compounds Ia or b) carrying out stage a) in the presence of water to obtain compounds Ib.

The starting compounds II and III are known or can be obtained by known methods, e.g. by electrochemical oxidation of cyclohexanone with alkanols in the presence of an auxiliary electrolyte and water and subsequent acid- or base-catalyzed methanol elimination (DE-A 4 017 576).

Among the defined compounds II and III, those preferred for economic reasons are the ones in which the radicals have the following meanings:

$R^1$, $R^2$ hydrogen;

$R^1$–$R^3$ $C_1$–$C_8$-alkyl, preferably $C_1$–$C_4$-alkyl, and of these preferably $C_1$–$C_2$-alkyl such as ethyl and, especially, methyl;

$C_2$–$C_8$-alkenyl, preferably $C_2$–$C_6$-alkenyl, and of these preferably $C_2$–$C_4$-alkenyl such as propenyl, butenyl and, especially, ethenyl;

$C_2$–$C_8$-alkynyl, preferably $C_2$–$C_6$-alkynyl, and of these preferably $C_2$–$C_4$-alkynyl such as propynyl, butynyl and, especially, ethynyl;

$C_3$–$C_8$-cycloalkyl, preferably $C_5$–$C_7$-cycloalkyl such as cyclopentyl, cycloheptyl and, especially, cyclohexyl;

$C_7$–$C_8$-arylalkyl, preferably phenylethyl and very especially benzyl;

aryl, preferably phenyl.

With regard to the required products I, particular preference is given to 2-hydroxycyclohexanone dimethyl ketal and 2-methoxycyclohexanone respectively.

The catalyst used in the novel process is palladium on zirconium oxide as carrier material.

The supported catalyst preferably has an active metal content of from 0.2 to 5, in particular 0.6 to 1.5, % of the total weight of carrier and catalytically active metal calculated as metal.

The novel catalyst has a BET surface area of from 10 to 300 $m^2$/g of catalyst, preferably 40 to 150 $m^2$. The average pore diameter is in the range from 2 to 100 nm, preferably in the range from 10 to 30 nm.

The pore volume is in the range from 0.1 to 1 ml/g of catalyst, preferably in the range from 0.2 to 0.5 ml/g of catalyst.

The crystal modification of the zirconium oxide used as carrier material is from 60 to 100%, preferably 70 to 90%, monoclinic.

The catalyst may be employed as 2 mm to 4 mm pellets or as tablets with a diameter of from 3 to 5 mm, and as chips with particle sizes of from 0.05 to 1 mm, preferably 0.1 to 0.5 mm as largest diameter, or as powder with particle sizes of from 0.05 to 0.5 mm, the powder also being suitable as fluidized bed catalyst.

The space velocity in a continuous process is from 0.001 to 1 kg, preferably 0.01 to 0.5 kg, of the compound II or III per kg of the catalyst and per hour.

It is economically very advantageous to employ the palladium catalyst in partially deactivated form because this results in higher product selectivities.

Suitable substances for partial poisoning of the catalyst are sulfur-, selenium- and/or tellurium-containing compounds, barium sulfate, and carbon monoxide, which are generally employed, or added to the catalyst during its preparation, in amounts of from 0.05 to 0.3, preferably 0.1 to 0.15, % of the weight of the compound II or III.

It may be expedient to suppress dehydration processes during the dehydrogenation by providing the catalyst with an aqueous solution of a base during the preparation. The aqueous solution of the base can be applied, for example, by spraying or impregnating the carrier. Preferred bases are alkali metal hydroxides such as sodium or potassium hydroxide solution, and particularly preferred bases are alkali metal carbonates such as sodium carbonate and, especially, potassium carbonate.

These are normally employed in amounts of from 50 to 300, preferably 100 to 250, % of the weight of palladium.

The catalyst used can be prepared by methods known per se. Thus, for example, the carrier $ZrO_2$ is treated with solutions of palladium compounds, basic compounds and deactivators such as sulfur compounds together or separately in any sequence. The carrier material can moreover be impregnated either superficially or else through and through.

The palladium compound can be converted into the active metallic form by a reduction in the gas phase or liquid phase or by thermal treatment. It is possible to use for the gas-phase reduction CO, $CH_4$ or $H_2$.

The novel catalyst differs from dehydrogenation catalysts previously disclosed by being able to achieve higher selectivities and longer useful lives.

The dehydrogenation is normally carried out at from 200 to 400° C., preferably 240 to 340° C., and very particularly preferably at 280 to 300° C. Since it is a gas-phase reaction, the temperature must be chosen to be high enough to ensure complete vaporization of the starting compounds II or III.

It is advisable for technical reasons to employ the 2-hydroxycyclohexanone dialkyl ketals II and the 2-alkoxycyclohexanones III in the form of solutions and to vaporize them together with the solvent. Preferred solvents for obtaining compounds Ia are dioxane and tetrahydrofuran. Particularly good results are obtained with methanol.

Preferred for obtaining compounds Ib is water, also in the form of mixtures with the abovementioned solvents.

The solutions generally contain from 10 to 80, preferably 20 to 50, % by weight of compounds II or III.

The reaction is expediently carried out under atmospheric pressure, but reduced or slightly elevated pressure can also be used, i.e. in the range from 10 mbar to 20 bar, for example.

The hold up times on the catalyst are normally from 0.1 to 60 seconds, usually from 1 to 5 seconds.

The reaction takes place in the gas phase, and a fixed bed reaction and a gas-phase reaction in a fluidized bed are suitable.

In order to maintain the catalyst activity during the dehydrogenation, it is advisable to use a carrier gas consisting of hydrogen or a mixture of hydrogen and nitrogen or argon.

An economically very advantageous embodiment of the novel process comprises a fixed bed reaction entailing vaporization of the 2-hydroxycyclohexanone dialkyl ketal II or the 2-alkoxycyclohexanone III, possibly in solution, and passing it in the gas phase, with or without the aid of a carrier gas, over a fixed catalyst.

The reaction products can be worked up in a manner known per se, as a rule by fractional distillation of the reaction mixture, with or without subsequent extraction.

The catechol monoethers Ia and catechols Ib which can be obtained in a simple and economical manner by the novel process can be used as intermediates for synthesizing drug products such as verapamil, or scents and flavorings such as vanillin.

The novel use of the $Pd/ZrO_2$ dehydrogenation catalyst is explained in detail in the following examples.

EXAMPLE 1

Catalyst Preparation

Catalyst A:

1248.8 g of $ZrO_2$ tablets (=1168.87 g $ZrO_2$) were sprayed with a solution of 24.96 g of Pd acetate (=11.8 g Pd) and 40.7 g of oxalic acid in 500 ml of water and dried at 950° C. for 16 h. After addition of a solution of 20.9 g of $K_2CO_3$.1.5 $H_2O$ (=11.91 g $K_2O$) in 500 ml of water, the tablets were again dried at 950° C. for 48 h. In the last step, the tablets were mixed with a solution of 6.38 g of 40% strength $(NH_4)_2S$ (=1.2 g S) in 510 ml of water and dried at 100° C. for 24 h.

The finished catalyst had a palladium content of 0.87% by weight, a potassium content of 0.81% by weight and a sulfur content of 0.09% by weight. The size of the palladium particles was, according to TEM (transmission electron microscopy), about 25 to 150 nm, and the size of the $ZrO_2$ particles was 10 to 20 nm. The total pore surface area was, according to Hg porosimetry, 92 $m^2$/g, the average pore diameter was 0.023 $\mu$m and the total pore volume was 0.388 ml/g. The BET surface area was 75 $m^2$/g.

Catalyst B:

757.9 g of $ZrO_2$ tablets (=730.62 g $ZrO_2$) were sprayed with a solution of Pd nitrate (=7.38 g Pd) in 182 ml of water and dried at 95° C. for 16 h. After addition of a solution of 13.09 g of $K_2CO_3$.1.5 $H_2O$ (=7.46 g $K_2O$) in 162 ml of water, the tablets were again dried at 95° C. for 48 h. In the last step, the tablets were mixed with a solution of 3.99 g of 40% strength $(NH_4)_2S$ (=0.75 g S) in 163 ml of water and dried at 100° C. for 24 h.

The finished catalyst had a palladium content of 0.93% by weight, a potassium content of 0.91% by weight and a sulfur content of 0.08% by weight. The size of the palladium particles was, according to TEM (transmission electron microscopy), about 3 to 10 nm, and the size of the $ZrO_2$ particles was 3 to 10 nm. The total pore surface area was, according to Hg porosimetry, 74 m²/g, the average pore diameter was 0.014 μm and the total pore volume was 0.228 ml/g.

Catalyst C:

200 g of $ZrO_2$ pellets (BET surface area 92 m²/g) were sprayed with a solution of 4.27 g of Pd acetate (=2.025 g Pd) and 5.6 g of oxalic acid in 55 ml of water and dried at 95° C. for 16 h. After addition of a solution of 3.61 g of $K_2CO_3 \cdot 1.5 H_2O$ (=2.06 g $K_2O$) in 55 ml of water, the pellets were again dried at 950° C. for 48 h. In the last step, the pellets were mixed with a solution of 1.1 g of 40% strength $(NH_4)_2S$ (=0.207 g S) in 55 ml of water and dried at 100° C. for 24 h.

The finished catalyst had a palladium content of 0.97% by weight, a potassium content of 0.98% by weight and a sulfur content of 0.13% by weight. The total pore surface area was, according to Hg porosimetry, 71 m²/g, the average pore diameter was 0.013 μm and the total pore volume was 0.23 ml/g.

Catalyst D:

200 g of $ZrO_2$ pellets (BET surface area 70 m²/g) were sprayed with a solution of 4.27 g of Pd acetate (=2.025 g Pd) and 5.6 g of oxalic acid in 55 ml of water and dried at 95° C. for 16 h. After addition of a solution of 3.61 g of $K_2CO_3 \cdot 1.5 H_2O$ (=2.06 g $K_2O$) in 55 ml of water, the pellets were again dried at 95° C. for 48 h. In the last step, the pellets were mixed with a solution of 1.1 g of 40% strength $(NH_4)_2S$ (=0.207 g S) in 55 ml of water and dried at 100° C. for 24 h.

The finished catalyst had a palladium content of 0.98% by weight, a potassium content of 0.94% by weight and a sulfur content of 0.11% by weight. The total pore surface area was, according to Hg porosimetry, 71 m²/g, the average pore diameter was 0.017 μm and the total pore volume was 0.29 ml/g.

Catalyst E (comparative catalyst as disclosed in DE-A-2 155 30 562: Example 1):

1000 g of silicon carbide were added as carrier to an aqueous solution of 300 g of Ni $(NO_3)_2 \cdot 6H_2O$, 75 g of $Cu(NO_3)_2 \cdot 3H_2O$, 9 g of $Cr(NO_3)_3 \cdot 9H_2O$, 0.6 g of $H_2SO_4$ and 0.35 g of $Na_2SO_4$. The resulting mixture was heated with stirring to evaporate off the water and subsequently calcined at 400° C. in a stream of air for 4 h.

EXAMPLE 2

Preparation of Catechol Monomethyl Ether from Dimethoxycyclohexanol

A methanolic solution consisting of 6 g/h of 2-hydroxycyclohexanone dimethyl ketal was vaporized at 300° C. and passed together with 60 l/h of a 1:1 mixture of hydrogen and nitrogen as carrier gas over the catalysts specified in Table 1. The resulting products were trapped and analyzed by gas chromatography. The useful life of the catalysts was defined as the time until the selectivity had fallen to 90% of the maximum selectivity achieved.

TABLE 1

| Catalyst | Temperature [° C.] | Conversion [%] | Selectivity [%] | WHSV[+) [h⁻¹] | Useful life [h] |
|---|---|---|---|---|---|
| A | 300 | 100 | 86 | 0.03 | 122 |
| A | 300 | 95 | 80 | 0.19 | 25 |
| B | 300 | 100 | 85 | 0.02 | 73 |
| C | 300 | 100 | 83 | 0.02 | 298 |
| D | 300 | 100 | 82 | 0.02 | 186 |
| E (Comparative) | 300 | 100 | 43 | 0.03 | 23 |
| F*) (Comparative) | 300 | 100 | 69 | 0.02 | 32 |
| G▽) (Comparative) | 300 | — | — | 0.02 | — |

+)WHSV = weight hourly space velocity [g/g·h]
*)Palladium on active carbon as disclosed in EP-A-0 499 055; Example 1 (Composition: 1% Pd, 1.5% $K_2CO_3$, 0.1% S).
▽)Palladium/chromium on lithium aluminum spinel, as described in DE 2064097 (Composition: 2% Li, 0.66% Pd, 0.98% Cr).

EXAMPLE 3

Preparation of Catechol Monomethyl Ether from Methoxycyclohexanone

A methanolic solution consisting of 6 g/h of 2-methoxycyclohexanone was vaporized at 300° C. and passed together with 60 l/h of a 1:1 mixture of hydrogen and nitrogen as carrier gas over the catalysts specified in Table 2. The resulting products were trapped and analyzed by gas chromatography. The useful life of the catalysts was defined as the time until the selectivity had fallen to 90% of the maximum selectivity achieved.

TABLE 2

| Catalyst | Temperature [° C.] | Conversion [%] | Selectivity [%] | WHSV [h⁻¹] | Useful life [h] |
|---|---|---|---|---|---|
| A | 300 | 100 | 90 | 0.07 | 372 |
| A | 360 | 93 | 88 | 0.12 | 47 |
| A | 300 | 97 | 85 | 0.22 | 21 |
| A | 300 | 86 | 88 | 0.31 | 27 |
| A | 300 | 99 | 82 | 0.46 | 10 |

EXAMPLE 4

Preparation of Catechol from Methoxycyclohexanone

A procedure similar to that in Example 3 but in aqueous solution resulted in comparable yields of catechol.

We claim:

1. A process for preparing catechol monoethers or catechols of the formula Ia or Ib

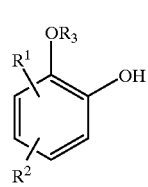

Ia

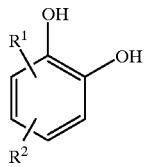

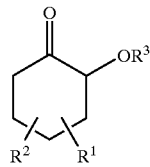

where $R^1$ and $R^2$ are, independently of one another, hydrogen or $C_1$–$C_8$-hydrocarbon radicals, and $R^3$ is a $C_1$–$C_8$-hydrocarbon radical, which comprises reacting a 2-hydroxycyclohexanone dialkyl ketal of the formula II or a 2-alkoxycyclohexanone of the formula III

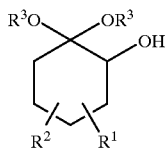

a) in the gas phase in the presence of palladium on zirconium oxide as catalyst, wherein the catalyst has a BET surface area of from 10 to 300 m$^2$/g of catalyst and a pore volume in the range from 0.1 to 1 ml/g of catalyst, to obtain compounds Ia or b) carrying out stage a) in the presence of water to obtain compounds Ib.

2. The process of claim 1, wherein the palladium on zirconium oxide catalyst has a BET surface area of from 40 to 150 m$^2$/g of catalyst and a pore volume in the range from 0.2 to 0.5 ml/g of catalyst.

3. The process of claim 1, wherein the crystal modification of the zirconium oxide used as carrier material is from 60 to 100% monoclinic.

4. The process of claim 1, wherein $R^1$ and $R^2$ are each hydrogen, and $R^3$ is methyl.

5. The process of claim 1, wherein a partially deactivated catalyst is employed.

* * * * *

UNITED STATES PATENT AND TRADEMARK OFFICE
CERTIFICATE OF CORRECTION

PATENT NO. : 6,013,844
DATED : January 11, 2000
INVENTOR(S) : HEINEKE et al.

It is certified that error appears in the above-identified patent and that said Letters Patent is hereby corrected as shown below:

Insert the following information on the cover page:

--[30] Foreign Application Priority Data
Jul. 15, 1997 [DE] Germany ............ 197 30 308.0--.

Signed and Sealed this

First Day of August, 2000

*Attest:*

*Attesting Officer*

Q. TODD DICKINSON

*Director of Patents and Trademarks*